United States Patent [19]

Hopp et al.

[11] Patent Number: 5,248,831
[45] Date of Patent: Sep. 28, 1993

[54] ETHERS OF 1-HYDROXY-HEX-5-EN-2-ONE, PROCESSES FOR THEIR PREPARATION AND THEIR USE AS ODORIFEROUS SUBSTANCES

[75] Inventors: Rudolf Hopp; Thomas Thielmann, both of Holzminden; Wilhelm Göttsch, Bevern, all of Fed. Rep. of Germany

[73] Assignee: Haarmann & Reimer GmbH, Holzminden, Fed. Rep. of Germany

[21] Appl. No.: 900,630

[22] Filed: Jun. 18, 1992

[30] Foreign Application Priority Data

Jun. 28, 1991 [DE] Fed. Rep. of Germany ....... 4121364

[51] Int. Cl.$^5$ ............................................. C07C 49/303
[52] U.S. Cl. ................................... 568/376; 568/308; 568/415; 512/20; 512/23; 512/25
[58] Field of Search .................... 568/376, 308, 415

[56] References Cited

FOREIGN PATENT DOCUMENTS 0803164 4/1954 United Kingdom ................ 568/412
1345081 6/1974 United Kingdom ................ 560/174

OTHER PUBLICATIONS

Chemical Abstracts, vol. 86, 1977, Abstract No. 170082g.
Kondo et al., Chem. Abst., vol. 1708,82g (1977).
J. Chem. Soc., by T. Kato et al., Perkin I(1979), pp. 529–532.

Primary Examiner—James H. Reamer
Attorney, Agent, or Firm—Sprung, Horn, Kramer & Woods

[57] ABSTRACT

Ethers of 1-hydroxy-hex-5-en-2-one are useful odoriferous substances which have a very complex fragrance pattern and allow an interesting variation in the scent of perfume oils.

3 Claims, No Drawings

ETHERS OF 1-HYDROXY-HEX-5-EN-2-ONE, PROCESSES FOR THEIR PREPARATION AND THEIR USE AS ODORIFEROUS SUBSTANCES

The invention relates to compounds of the formula

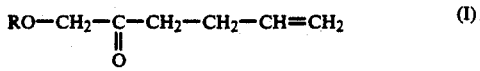

$$RO-CH_2-C(=O)-CH_2-CH_2-CH=CH_2 \quad (I)$$

wherein
R denotes optionally substituted alkyl, optionally substituted cycloalkyl, optionally substituted aralkyl or optionally substituted aryl,
and to processes for the preparation of these compounds from ethers of 4-hydroxy-acetoacetic acid esters by alkenylation with allyl halide and hydrolysis and decarboxylation of the reaction products.

The term "alkyl" represents straight-chain or branched alkyl having preferably 1 to 12 C atoms, such as methyl, ethyl, n- and i-propyl, n-, sec-, i- and tert-butyl, n-, i- and tert-pentyl, n-hexyl, i-octyl, i-nonyl, n-decyl and n-dodecyl. These alkyl groups can be substituted by 1 to 3 halogen atoms, preferably chlorine and/or fluorine, or by a $C_1-C_6$-alkoxycarbonyl group. Substituted alkyl groups accordingly include, for example, mono-, di- and trifluoromethyl, monochlorodifluoromethyl and methoxy- and ethoxycarbonylmethyl.

The term "cycloalkyl" includes cycloalkyl having preferably 3 to 7 C atoms, in particular 5 or 6 C atoms, such as unsubstituted or substituted cyclopropyl, cyclobutyl, cyclopentyl, cyclohexyl and cycloheptyl.

"Aralkyl" contains preferably 1 to 6, in particular 1 to 4, C atoms in the straight-chain or branched alkyl part and preferably 6 to 12 C atoms, in particular phenyl or naphthyl, as the aryl part. Examples of such aralkyl groups include benzyl, α-methylbenzyl, α,α-dimethylbenzyl, 2-phenethyl and α- and β-naphthylmethyl. These aralkyl radicals can carry 1 to 3 substituents from the series comprising halogen (in particular chlorine and/or fluorine), nitro, cyano, optionally halogenated $C_1-C_4$-alkyl or -alkoxy, such as, for example, methyl, ethyl, trifluoromethyl, difluorochloromethyl, difluoromethyl, trichloromethyl, methoxy, ethoxy, trifluoromethoxy, difluorochloromethoxy and difluoromethoxy, and optionally halogenated $C_1-C_4$-alkylmercapto, such as, for example, methylmercapto, trifluoromethylmercapto and difluorochloromethylmercapto.

The term "aryl" includes unsubstituted or substituted aryl having preferably 6 to 10 carbon atoms in the aryl part. Radicals which may be mentioned as examples and as preferred are unsubstituted or substituted phenyl or naphthyl, in particular phenyl.

Substituents which are suitable for substituted aryl radicals include, for example, halogen, cyano, nitro, hydroxyl, amino, mercapto, straight-chain or branched alkyl having 1 to 6 carbon atoms, straight-chain or branched halogenoalkyl having 1 to 6 carbon atoms and 1 to 13 identical or different halogen atoms, in each case straight-chain or branched alkoxy or alkylthio having in each case 1 to 6 carbon atoms, in each case straight-chain or branched halogenoalkylthio or halogenoalkoxy having in each case 1 to 6 carbon atoms and in each case 1 to 13 identical or different halogen atoms, in each case straight-chain or branched alkenyl or alkinyl having 2 to 6 carbon atoms, in each case straight-chain or branched alkenyloxy or alkinyloxy having 2 to 6 carbon atoms, cycloalkyl having 3 to 8 carbon atoms and phenyl, phenoxy, phenylthio, phenylalkylthio or phenylalkoxy having in each case 1 to 4 carbon atoms in the straight-chain or branched alkyl part.

The compounds I according to the invention can be prepared in accordance with the following equation, wherein X represents halogen (for example bromine, chlorine or iodine), R has the abovementioned meaning and R' independently of R can assume the meanings given above for R.

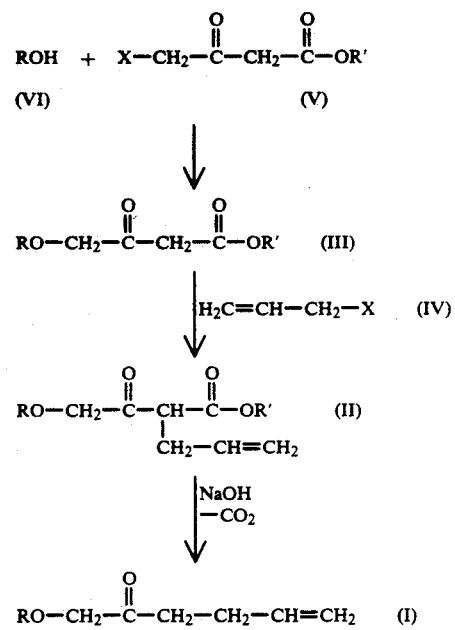

The compounds (I) according to the invention which can be used as odoriferous substances are accessible by hydrolysis and decarboxylation of 4-organooxy-α-allylacetoacetic acid esters (II), which can be prepared from the corresponding 4-organooxy-acetoacetic acid esters (III) and allyl halide (IV). The compounds (III) in turn are known at least in some cases, and can be prepared from 4-halogeno-acetoacetic acid esters (V) and alcohols or phenols (VI) in the presence of strong bases or from (V) and alcoholates or phenolates, as described, for example, by T. Kato et al., J. Chem. Soc., Perkin I (1979), 529, or by analogous processes.

In detail, the alcoholates or phenolates to be used for this reaction can be prepared from the alcohols or phenols (VI) in the customary manner by reaction with alkali metals, preferably lithium, sodium or potassium. The alcohols or phenols (VI) can serve as solvents for this operation and for the further reaction. As mentioned, the reaction of the 4-halogeno-acetoacetic acid esters (V) can also be carried out in the presence of strong bases, such as, for example, alkali metal amides, alkali metal hydrides or complex hydrides, such as sodium borohydride, suitable alcoholates or amines.

Bromine or iodine can also serve as halogen in the compounds (V); however, chlorine is preferred merely for reasons of costs alone.

The molar ratio (V)/(VI) is as a rule 1:1.5 to 1:0.1, preferably 1:1.1 to 1:0.5. The presence of organic dipolar aprotic solvents, such as dimethyl sulphoxide and preferably dimethylformamide, may be advantageous for the reaction. The reaction can be carried out at temperatures from 0° to 150° C., preferably 20° to 80° C. A quantitative conversion is as a rule awaited, and the mixture is then worked up in the customary manner, that is to say the solvent is stripped off, the residue is neutralised or rendered acid with aqueous mineral acid, the reaction product is extracted with an organic solvent, the solvent is stripped off and if appropriate the residue is further purified, for example by distillation.

Molar ratios of (IV)/(III) of 3:1 to 0.5:1, preferably 1.2:1 to 0.9:1, are in general chosen for the reaction of the 4-organooxy-acetoacetic acid ester (III) thus obtained with the allyl halide (IV). Since the reaction proceeds exothermically, it is advisable to cool the reaction mixture first, so that its temperature as far as possible does not exceed 200° C., preferably 60° C. For a quantitative reaction, the reaction mixture should be left at a temperature of 30° to 200° C., preferably 50° to 60° C., for a further 0.5-24 hours, preferably 1-5 hours, when the addition of (IV) has ended. The reaction can be carried out in the presence of the bases and solvents mentioned above for the reaction between the compounds (V) and (VI). The reaction mixture can be worked up as described for the synthesis of the 4-organooxy-acetoacetic acid ester (III).

The hydrolysis and decarboxylation of the resulting α-allyl-acetoacetic acid ester (II) are best carried out in aqueous sodium hydroxide solution or potassium hydroxide solution at temperatures between 70 and 160, preferably 90° and 140° C. The amount of alkali is calculated such that at least 1 mol, but preferably 1.5 to 5 mol, of alkali metal hydroxide is present per mol of ester (III). A water-miscible alcohol, such as, for example, ethanol, can be co-used for better miscibility. The decarboxylation starts spontaneously at the abovementioned temperatures, at the rate at which the hydrolysis progresses. The desired reaction product (I) can be extracted with an organic solvent and isolated from this by stripping off the solvent. A distillation can follow for purification.

The invention thus furthermore relates to compounds of the formula (II)

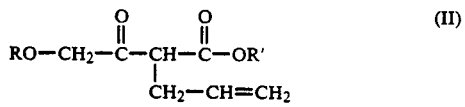

wherein R and—independently of R—R' have the meaning given above under R.

The invention furthermore relates to a process for the preparation of the compounds (II) by reaction of the compounds (III) with allyl halide, and finally the invention relates to a process for the preparation of the compounds (I) by hydrolysis and decarboxylation of the compounds (II).

The compounds (I) according to the invention are odoriferous substances which have a very complex fragrance pattern and allow an interesting variation in the scent of perfume oils. Since the compounds (I) also have a very strong fragrance, good effects can already be achieved by addition of small amounts.

Some examples of scent descriptions are as follows:

1-Cyclohexyloxy-hex-5-en-2-one: Odoriferous substance having a very fruity galbanum note. The main notes are very reminiscent of galbanum oil and pineapple. Woody and herbaceous notes reminiscent of camomile and straw are also found. The pineapple note is accompanied by fig-, rum- and arrack-like nuances. A slightly animal civet-like note is also found. - This highly fragrant odoriferous substance combines fragrance notes which can otherwise be achieved only by mixing several odoriferous substances.

1-(3-Methylcyclohexyloxy)-hex-5-en-2-one: Highly fragrant and clinging odoriferous substance having herbaceously green nuances reminiscent mainly of camomile, valerian, basil and galbanum. The fruity nuances are reminiscent of the fragrance of dried fruits and pineapple. Flowery, violet-like elements can also be detected.

The compounds (I) according to the invention can be used combination with other odoriferous substances which are known per se (Arctander, Perfume and Flavor Chemicals, Montclair, N.J. (USA), 1969) and essential oils which are known per se (Arctander, Perfume and Flavor Materials of Natural Origin, Elisabeth, N.J. (USA), 1960) and lead to perfume bases and odoriferous substance combinations which have highly expressive notes and are outstandingly suitable for perfuming finished products in the aerosol, detergent and chemicals sector, but in particular the fine perfumery and cosmetics sector, for example for detergents, hair care agents, bubblebaths, bath salts, dishwashing agents, washing powders, soaps, antiperspirants, powders, creams, shaving lotions, after-shave lotions, air fresheners, WC cleaners, room sprays, antiperspirant sprays, deodorant sprays, body sprays and sunscreen agents.

The amount added to perfume oils is between 0.1 and 10% by weight, but preferably between 0.5 and 3% by weight, based on the perfume oil (before the addition). The perfume compositions and perfumed products can be prepared in the customary manner, for example by bringing the components together.

Unless stated otherwise, the percentage data in the following examples relate to the weight.

EXAMPLE

Example 1 a) 320 g of ethyl 4-cyclohexyloxy-acetoacetate (1.4 mol) are initially introduced into a threenecked flask fitted with a stirrer, dropping funnel, drying tube and reflux condenser, and an Na ethanolate solution prepared from 32 g of sodium (1.4 mol) and 475 g of ethanol is added at 50° C. in the course of 30 minutes. 170 g of allyl bromide (1.4 mol) are then metered in at 50°-60° C. in the course of 30 minutes, while cooling. The mixture is subsequently stirred at 50° C. for 2 hours, the ethanol is then distilled off and the reaction mixture which remains is brought to pH=3 with hydrochloric acid. After the phases have been separated, the aqueous phase is extracted twice with 750 ml of toluene each time, the organic phases are combined and concentrated and the residue is distilled. Ethyl 2-(cyclohexyloxyacetyl)-4-pentenoate is obtained. (Temperature (bottom)=152°-179° C., temperature (top)=102°-127° C.; 1 mbar).

b) 140 g of ethyl 2-(cyclohexyloxyacetyl)-4-pentenoate are heated under reflux in 650 g of 5% strength aqueous sodium hydroxide solution for 4 hours. 500 ml of ether are added to the reaction mixture. The organic phase is separated off and concentrated and the residue is distilled. About 60 g of 1-cyclohexyloxy-hex-5-en-2-one are obtained. (Temperature (bottom)=115°-155° C., temperature (top)=83° C.; 0.8 mbar).

Example 2

1-(3-Methyl-cyclohexyloxy)-hex-5-en-2-one was prepared analogously to Example 1; boiling point 103° C./2 mbar.

Use

An odoriferous substance composition having a flowery green fragrance is prepared by mixing the following constituents (amount data in grams):

| | |
|---|---|
| Hexenyl salicylate | 80 |
| Orange oil cold-pressed | 30 |
| Muguet 10689 F (lily of the valley synth.) | 100 |
| Jasmin 10400 (jasmin synth.) | 100 |
| Bergamot oil synthessence | 100 |
| Dimethylbenzylcarbinyl acetate | 30 |
| γ-Iraldein | 80 |
| Linalyl acetate | 40 |
| Coumarin | 30 |
| Musk ketone | 60 |
| Phenylethyl alcohol | 80 |
| Isoeugenol | 4 |
| Eugenol | 6 |
| p-tert-Butylcyclohexyl acetate | 20 |
| o-tert-Butylcyclohexyl acetate | 20 |
| Ethylvanillin | 2 |
| Cyclopentadecanolide 50% | 30 |
| para-Hydroxybenzyl acetone | 1 |
| Undecylenealdehyde | 1 |
| Hexenyl acetate | 2 |
| Citral diethyl acetal | 10 |
| Evernyl | 4 |
| -continued | |
| Galbanum synthresin | 5 |
| Paraguay petitgrain oil | 15 |
| Diethyl phthalate | 140 |
| 1-Cyclohexyloxy-hex-5-en-2-one | 10 |
| | 1,000 |

The addition of 1% 1-cyclohexyloxy-hex-en-2-one changes the fragrance pattern such that a more usefully expectant composition is formed such as can otherwise be achieved only by addition of very expensive natural blossom or balsam extracts. The example described is thus rounded off, by addition of 1% of the above ketone, with a sweetfruity note which suggests a connection with flowery chypre and oriental fragrances and significantly improves olfactory acceptance.

We claim:
1. A compound of the formula

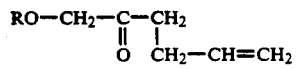

in which
R is cyclohexyl or methylcyclohexyl.
2. A compound according to claim 1 wherein the compound is 1-cyclohexyloxy-hex-5-en-2-one.
3. A compound according to claim 1 wherein the compound is 1(3-methyl-cyclohexyloxy)-hex5-en-2-one.

* * * * *